(12) United States Patent
Neff et al.

(10) Patent No.: US 9,482,600 B2
(45) Date of Patent: Nov. 1, 2016

(54) SAMPLE COLLECTION UNIT, SYSTEM AND METHOD FOR MICROBIOLOGICAL AIR ANALYSIS

(71) Applicant: Robert Bosch GmbH, Stuttgart (DE)

(72) Inventors: Petra Neff, Stuttgart (DE); Mike Uhlig, Stuttgart (DE); Andreas Neumann, Eningen Unter Achalm (DE)

(73) Assignee: Robert Bosch GmbH, Stuttgart (DE)

( * ) Notice: Subject to any disclaimer, the term of this patent is extended or adjusted under 35 U.S.C. 154(b) by 416 days.

(21) Appl. No.: 13/888,019

(22) Filed: May 6, 2013

(65) Prior Publication Data
US 2013/0298641 A1    Nov. 14, 2013

(30) Foreign Application Priority Data
May 10, 2012  (DE) .................. 10 2012 207 796

(51) Int. Cl.
*G01N 1/00*    (2006.01)
*G01N 1/22*    (2006.01)
*G01N 1/38*    (2006.01)

(52) U.S. Cl.
CPC ............ *G01N 1/2273* (2013.01); *G01N 1/2214* (2013.01); *G01N 1/38* (2013.01)

(58) Field of Classification Search
CPC .... G01N 1/2214; G01N 1/2273; G01N 1/38; G01N 1/405; G01N 23/22; G01N 30/8668; G01N 21/274; G01N 27/622; H01J 49/049; H01J 49/0027; G08B 21/182

USPC ............. 73/863, 863.12, 31.01, 23.2, 31.25, 73/23.41; 156/345.32
See application file for complete search history.

(56) References Cited

U.S. PATENT DOCUMENTS 6,091,483 A * 7/2000 Guirguis ............. G01N 1/4077
356/36
2009/0193911 A1* 8/2009 Mileham ............. G01N 1/2211
73/863.02

FOREIGN PATENT DOCUMENTS

DE        102 32 850 A1    2/2004

* cited by examiner

*Primary Examiner* — Lisa Caputo
*Assistant Examiner* — Brandi Hopkins
(74) *Attorney, Agent, or Firm* — Maginot, Moore & Beck LLP

(57) ABSTRACT

A sample collection unit for microbiological air analysis includes a housing and a sample treatment path. The housing has a sample inlet opening, an optical window, and an air outlet opening. The sample treatment path has a conjugation pad, and a test strip with a test area and an absorber section. The sample collection unit also has a device configured to receive a container for a solvent, and a device configured to release the solvent. The sample collection unit is preferably configured as a disposable component in the form of a cartridge. Integration of the container for the solvent in the sample collection unit permits simplification and automation of the corresponding sampling method.

15 Claims, 2 Drawing Sheets

SAMPLE COLLECTION UNIT, SYSTEM AND METHOD FOR MICROBIOLOGICAL AIR ANALYSIS

This application claims priority under 35 U.S.C. §119 to patent application no. DE 10 2012 207 796.0, filed on May 10, 2012 in Germany, the disclosure of which is incorporated herein by reference in its entirety.

The present disclosure relates to a sample collection unit, a system and a method for microbiological air analysis.

BACKGROUND

Air sampling systems for microbiological analysis are known that consist of an air delivery unit and of a collector head. Systems for this purpose are sold, for example, by the company called Umweltanalytik Holbach GmbH. Particles can be collected, for example by means of slot jet impingement, on adhesively coated slides. After the particles have been collected, the slides are removed, sent to the analysis site and examined microscopically there, and the deposited microorganisms are identified and counted.

These air sampling systems or air analysis systems require a relatively high outlay, both in terms of the equipment and also in terms of the amount of work.

DE 102 32 850 A1 discloses a mobile analyzing device for gas analysis. Sample quantities of the gas are brought into contact with an analyte in order to trigger an analysis reaction and can be condensed to the liquid phase by means of a thermocouple and then analyzed.

SUMMARY

The present disclosure proposes a sample collection unit according to the description below, a system according to the description below, and a method according to the description below, in each case for microbiological air analysis.

Accordingly, provision is made as follows:

A sample collection unit for microbiological air analysis has a housing and a sample treatment path. The housing has a sample inlet opening, an optical window, and an air outlet opening, and the sample treatment path has a conjugation pad, a test strip with a test area, and an absorber section. The sample collection unit also has a device for receiving a container for a solvent, and a device for releasing the solvent.

A system for microbiological air analysis has a sampling unit and an analysis unit, wherein the above-described sample collection unit is both part of the sampling unit and also part of the analysis unit.

Moreover, a method for microbiological air analysis is provided, with the following method steps: a) building a sampling unit with a sample collection unit, b) collecting particles in the sample collection unit, c) building an analysis unit with the sample collection unit, d) releasing a solvent in the sample collection unit, e) transporting the particles into a test area by means of the solvent, and f) analyzing the particles in the test area in the analysis unit.

In the preferred embodiment of the disclosure, the sample collection unit is configured as a cartridge, in particular as a disposable cartridge.

Preferred refinements form the subject matter of the description below.

According to the disclosure, by arrangement of a container for a solvent and of a device for release of the solvent in the sample collection unit, an analysis of the air sample can take place in the sample collection unit. Compared to the prior art, more standardized components are used, in particular a sample collection unit preferably configured as a cartridge, and method steps previously carried out manually are omitted.

A possibility is afforded by which particles are collected from the air and the collected particles are then transferred to a liquid phase in an automated manner, e.g. in order to be able to then analyze the dissolved particles. Automation that includes the analysis is also possible.

In the context of this application, the term "conjugation pad" means an element or a device that is configured to specifically bind the target analyte and to release the latter, through addition of the solvent, for analysis.

It is also advantageous if the device for receiving a container for a solvent has a container integrated in the sample collection unit. This measure permits simplified handling of the solvent container and safe handling of the solvent, and it reduces the amount of solvent compared to traditional methods.

Moreover, it is advantageous if the container has a predetermined breaking point. This measure permits safe and simplified handling by mechanical addition of the solvent.

It is furthermore advantageous if the device for releasing the solvent has an actuation mechanism with a plunger or spike movable toward the container. This measure likewise permits safe and simplified handling by mechanical addition of the solvent.

In addition, it is advantageous if the actuation mechanism can be actuated from outside the sample collection unit. This measure permits direct operation by the user after the collection procedure has ended. Moreover, this can be carried out at a different time from the collection procedure.

It is also advantageous if the conjugation pad has an adhesive that is soluble in the solvent. By means of this measure, the adhesive temporarily binds the collected sample on the pad, such that the sample, including the adhesive, can be detached from the pad by addition of the solvent.

It is also advantageous if the sample collection unit has a plurality of parallel test strips. This measure permits simultaneous examination of the sample on different analytes (one analyte per test strip) or multiple use in one sample collection unit.

It is also advantageous if the test strip has a reference area. In this way, the result of the unknown sample can be compared with a reference sample.

It is also advantageous if the sample inlet opening, the optical window and/or the air outlet opening have a film which is removable before use of the sample collection unit. In this way, the sample collection unit is protected, prior to use, against contamination and damage to the listed areas. Optionally, an opaque film can be provided in order to protect the light-sensitive interior of the sample collection unit.

Moreover, it is advantageous if the optical window is surrounded by an opaque sealing lip. This measure permits screening against extraneous light.

It is furthermore advantageous if the sample collection unit is configured as a cartridge. In this way, the sample collection unit is exchangeable and easy to handle.

It is also advantageous if the cartridge has catches for locking it onto a sampling unit and/or an analysis unit. In this way, it is possible to fix the units to each other and provide product protection through the form of the catches (no foreign cartridges).

It is also advantageous if the sample collection unit has a device for releasing a solvent, which device has an actuation mechanism coupled to the catches. By this measure, accidental activation of the release procedure is avoided, since the catch allows solvent to be added only during simultaneous use of the analysis unit, as a result of which a loss of sample material in the absence of the analysis unit is prevented.

BRIEF DESCRIPTION OF THE DRAWINGS

The present disclosure is explained in more detail below on the basis of the illustrative embodiments shown in the schematic figures of the drawings.

Figure 1:
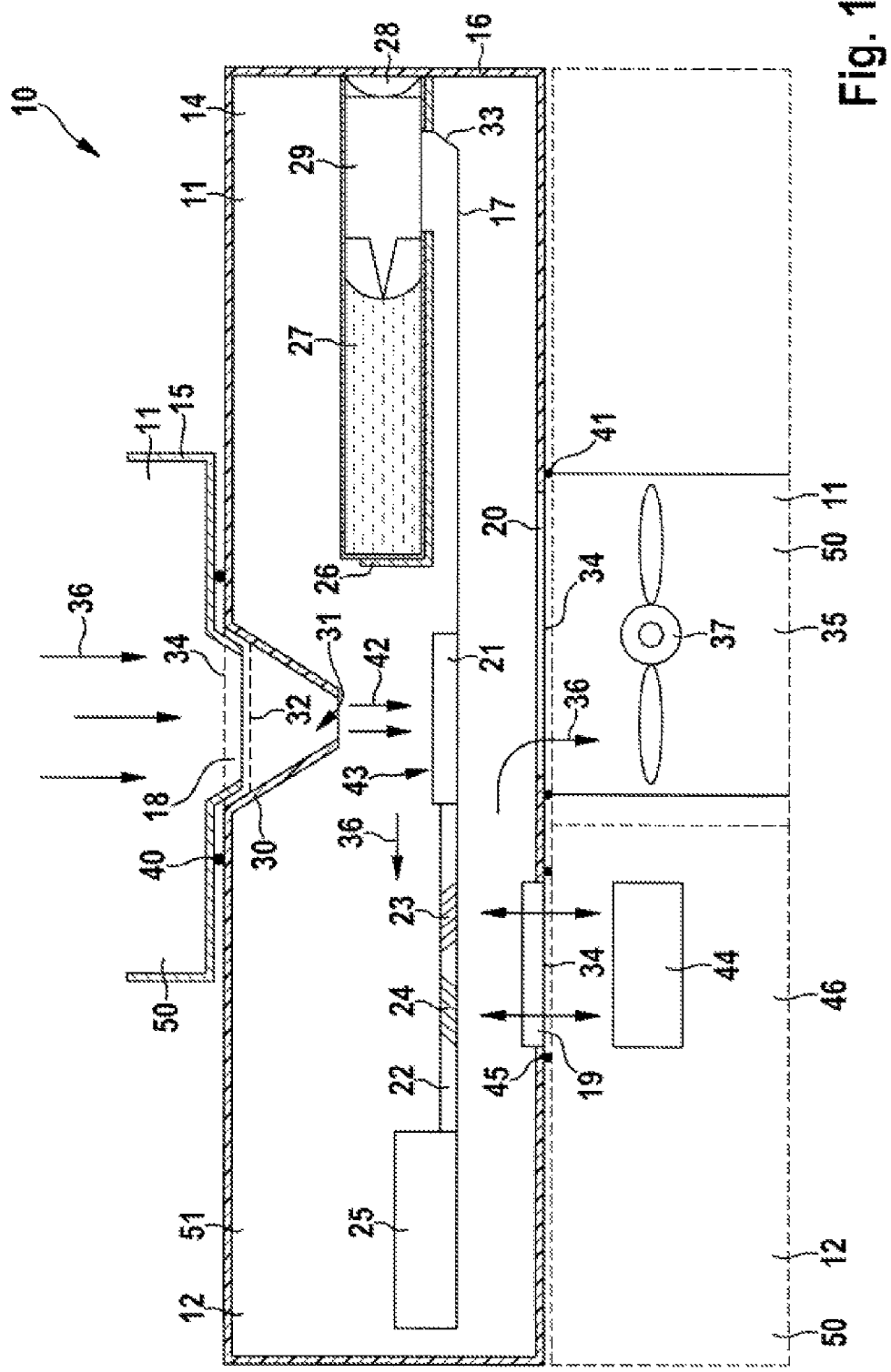
FIG. 1 shows a schematic view of a system with a sample collection unit for microbiological air analysis according to one embodiment of the present disclosure.

The attached drawings are intended to provide greater understanding of the embodiments of the disclosure. They depict embodiments and, together with the description, serve to explain the principles and concepts of the disclosure. Other embodiments and many of the stated advantages will become clear from the drawings. The elements in the drawings are not necessarily shown true to scale in relation to one another.

DETAILED DESCRIPTION

FIG. 1 shows a system 10 for microbiological air analysis according to one embodiment of the present disclosure. The system 10 has a sampling unit 11 and an analysis unit 12. Here, a sample collection unit 14 is both part of the sampling unit 11 and also part of the analysis unit 12.

The sampling unit 11 has, in addition to the sample collection unit 14, an optional sample collector head 15, which is made of metal and which is arranged on the sample collection unit 14 and, during operation of the system 10, forms a defined air inlet.

The sample collection unit 14 has a housing 16 and a sample treatment path 17. The housing 16 is a plastic injection-molded part and is here configured as a disposable component. The housing 16 has a sample inlet opening 18, an optical window 19, and an air outlet opening 20.

The sample treatment path 17 has a conjugation pad 21 in the form of a baffle plate, and a test strip 22 with a test area 23, a reference area 24 and an absorber section 25. The conjugation pad 21 is arranged in direct proximity to the test strip or is alternatively part of the test strip.

The sample treatment path 17 also has a device 26 for receiving a container 27 for a solvent, and a device 28 for releasing the solvent, with a plunger or spike 29. In the embodiment shown, the container 27 is integrated in the sample collection unit 14. The container 27 can have a predetermined breaking point. The plunger or spike 29, movable toward the container 27, is part of an actuation mechanism of the device for releasing the solvent. The actuation mechanism can be actuated from outside the sample collection unit.

The sample treatment path 17 also has a liquid guide 33 which, during operation, guides the solvent, after the release thereof from the container 27, via the conjugation pad 21 and the test strip 22 to the absorber section 25 thereof.

The housing 16 is shaped around the sample inlet opening 18 in such a way that an air guide channel 30 is formed with an air guide slot 31 which is arranged over the conjugation pad 21. The air guide channel 30 is configured to receive an alternative pre-filter 32. With the pre-filter 32, particles above a selectable size can be removed from the air sample before the analysis.

Before insertion into the sampling unit 11, the housing 16 of the sample collection unit 14 has a protective film on the sample inlet opening 18, on the optical window 19 and on the air outlet opening 20, at the positions 34.

The sampling unit 11 also has a device 35 for generating an air flow 36, in this case a fan 37. The device 35 can optionally have a volumetric flow meter (not shown). In the embodiment shown, sealing lips 40, 41 are arranged between the sample collector head 15 and the sample collection unit 14 and, respectively, between the sample collection unit 14 and the device 35 for generating an air flow, which sealing lips 40, 41 can be formed on the sample collection unit 14, for example.

To carry out a sampling procedure, the sampling unit 11 is first of all assembled from its reusable components, namely the sample collector head 15 and the device 35 for generating an air flow, and from the disposable component, namely the sample collection unit 14. The reusable components, namely the sample collector head 15 and the device 35 for generating an air flow, can in this case already form a unit onto which the sample collection unit 14 can be detachably locked. Alternatively, sample collector head 15, sample collection unit 14 and device 35 can be connected to one another as separate components by means of catches.

During operation, the air flow 36 is generated by the device 35 such that particles from the air sample make contact, as per arrows 42, with the conjugation pad 21 and remain attached there. For this purpose, the conjugation pad 21 is provided with an adhesive layer 43 comprising an adhesive that is soluble in the solvent. The air flow 36 is deflected sideways on the conjugation pad 21 and flows around the sample treatment path 17 and through the air outlet opening 20 of the sample collection unit 14 into the device 35 for generating an air flow. The sampling procedure is ended when a sufficiently large quantity of air has flowed through the sampling unit 11.

The analysis unit 12 has a sensor device 44 with an optical transmitter and an optical receiver, which sensor device 44 is arranged under the optical window 19 of the sample collection unit 14. The sensor device 44 is arranged in a sensor part 46 which, together with the sample collection unit 14, forms the analysis unit 12. A lightproof sealing lip 45 made of rubber is arranged all around the optical window 19 and can be secured, for example, on the sensor part 46 in order to screen off ambient light during the analysis.

The sensor device 44 serves for the optical analysis of the test area 23 and of the reference area 24. For this purpose, two pairs composed of an optical transmitter and of an optical receiver can be directed respectively to the test area 23 and to the reference area 24. Alternatively, the sensor device 44 has only one optical transmitter and only one optical receiver and, during the measurement, either the sensor device is moved between the test area 23 and the reference area 24 or the test strip is moved with respect to the sensor device 44, which movement of the test strip can take place in the sample collection unit 14 or together with the sample collection unit 14.

To perform an analysis, the analysis unit 12 is first of all assembled from its reusable component, namely the sensor part 46, and from the disposable component, namely the sample collection unit 14, with the sensor part 46 and the sample collection unit 14 being connected to each other by means of catches.

Figure 2:
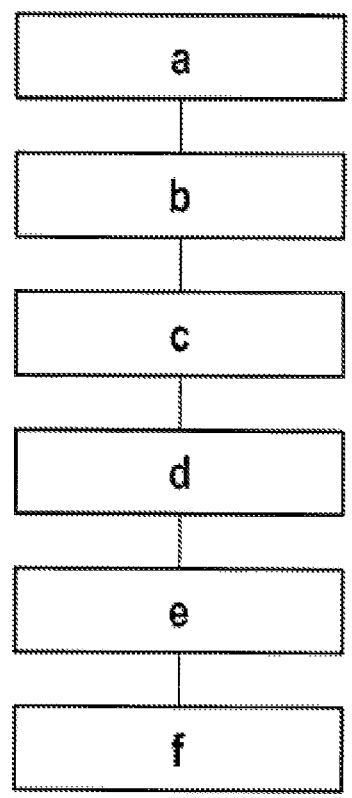
FIG. 2 shows a flow chart of the method for microbiological air analysis according to a further embodiment of the present disclosure.

FIG. 2 shows a flow chart of the method for microbiological air analysis according to a further embodiment of the present disclosure. The performance of a microbiological air analysis is now described using the example of the system 10 from FIG. 1, in which sample collection and analysis are initially described as separate, possibly spatially discrete procedures.

The method begins with method step a) building the sampling unit 11 with the sample collection unit 14, i.e. the assembly of the sampling unit 11 from its reusable components, namely the sample collector head 15 and the device 35 for generating an air flow, and from the disposable component, namely the sample collection unit 14. The protective films on the sample inlet opening 18 and on the air outlet opening 20 are removed. The sample collection unit 14 is preferably a cartridge, which is locked onto the other components.

Then, in method step b), particles are collected in the sample collection unit 14. The slow particles in the flow of air impact the conjugation pad 21 and attach to the adhesive layer 43 thereof.

Thereafter, in method step c), the analysis unit 11 is built with the sample collection unit 14. For this purpose, the catches of the sampling unit 11 are undone, if necessary, and the sample collection unit 14 is transported to the place of the analysis. The protective film on the optical window 19 is removed. The analysis unit 12 is assembled from its reusable component, namely the sensor part 46, and from the disposable component, namely the sample collection unit 14, and the sensor part 46 and sample collection unit 14 are connected to one another by means of catches.

Thereafter, in method step d), a solvent is released in the sample collection unit. For this purpose, a plunger or spike is actuated manually or by a motor of the analysis unit 11 or by an actuation mechanism coupled to the catches, and the container is broken open at a predetermined breaking point.

In method step e), the particles collected in b) are transported into the test area 23 of the test strip 22 by means of the solvent. The released solvent is guided to the conjugation pad 21 and dissolves the adhesive layer 43. The particles then go into solution or suspension, and the solvent, serving as transporting liquid, takes up the particles and transports them to the test area 23. The solvent mainly collects in the absorber section 25 of the test strip 22.

In method step f), the particles in the test area 23 of the test strip 22 are analyzed in the analysis unit 12 by means of the sensor device 44. A reference measurement on the reference area 24 of the test strip 22 can take place before or after the analysis of the test area 23. Optical detection is possible by absorption or fluorescence. The catch is then released, and the sample collection unit 14 is disposed of.

Following the description of the mode of operation, particular embodiments are now highlighted. The compact and modular structure permits an embodiment of the disclosure in which the reused components are brought together in an analysis appliance 50. In FIG. 1, such an analysis appliance comprises the sample collector head 15, the device 35 for generating an air flow, and the sensor part 46. The sample collection unit 14 configured as cartridge 51 is inserted into this analysis appliance 50. Sampling and analysis are possible one after another either without moving the sample collection unit 14 as in analysis appliance 50 or by simply changing the sample collection unit 14 around.

If the analysis appliance is configured such that the cartridge 51 of the sample collection unit 14 is in the same position during sampling and analysis, this analysis appliance, in a preferred embodiment, is configured such that a motor of the analysis appliance moves the plunger or spike 29 toward the container 27 and in so doing breaks open the container and releases the solvent. This analysis appliance is preferably controlled by a control unit, such that sample collection and analysis take place automatically. For the following sample examination, only the cartridge 51 has to be changed and, if appropriate, the sample collector head 15 examined for contamination.

As regards the method according to the disclosure, it should be noted, in this embodiment, that method step c) coincides with method step a), and both method steps take place before method step b).

If the analysis appliance is configured such that the sample collection unit 14 is changed around between sampling and analysis, this analysis appliance is preferably configured in such a way that, when the sample collection unit 14 is changed around, an automatic actuation mechanism moves the plunger or spike 29 toward the container 27 and in so doing breaks open the container and releases the solvent. The actuation mechanism can advantageously be coupled to catches.

In a particularly simple embodiment, the sample collector head 15 can be omitted. Moreover, a disposable component can be fitted into an air collection system, e.g. a pump or a fan. In an alternative minimal embodiment, the device 35 has only an attachment piece for connection of a vacuum cleaner. Regulation to a defined volumetric flow during collection is therefore not possible, but the air flow can nevertheless be limited by a bottleneck in the flow path.

The conjugation pad 21, on which the particles are collected, is composed either of a solid material, with the air flowing around the latter, or of a sponge-like material, which it is possible for the air to flow through.

In a further embodiment, the container with the solvent is placed separately into the equipment. A second cartridge can advantageously contain solvent for one or more measurements.

According to a further embodiment, instead of using a single test strip, particles are deposited sequentially onto a plurality of parallel test strips. After the last sample collection, one or more containers are then opened, from which solvent is released and reaches the test strips. The test strips are then analyzed in parallel or sequentially. Test strips and sensor device are suitably positioned relative to one another. In the case of movement of the test strips, either the test strips in the sample collection unit are moved or the sample collection unit is moved, preferably with position catches at the interval of the test strips. The sample collection unit can accordingly have a plurality of sample inlet openings.

Although the present disclosure has been described in full above on the basis of preferred illustrative embodiments, it is not limited to these and can instead be modified in various ways.

What is claimed is:
1. A sample collection unit for microbiological air analysis, comprising:
    a housing having a sample inlet opening, an optical window, and an air outlet opening;
    a sample treatment path having a conjugation pad, and a test strip with a test area and an absorber section, the test area located between the conjugation pad and the absorber section along the sample treatment path;
    a device configured to receive a container for a solvent; and a device configured to release the solvent into the sample treatment path so as to move a sample collected at the conjugation pad from the conjugation pad to the test area.

2. The sample collection unit according to claim 1, wherein the device configured to receive a container for a solvent has a container integrated in the sample collection unit.

3. The sample collection unit according to claim 2, wherein the container has a predetermined breaking location.

4. The sample collection unit according to claim 2, wherein the device configured to release the solvent has an actuation mechanism with a plunger configured to move toward the container.

5. The sample collection unit according to claim 4, wherein the actuation mechanism is configured to be actuated from outside the sample collection unit.

6. The sample collection unit according to claim 1, wherein the conjugation pad has an adhesive that is soluble in the solvent.

7. The sample collection unit according to claim 1, further comprising a plurality of parallel test strips.

8. The sample collection unit according to claim 1, wherein the test strip has a reference area.

9. The sample collection unit according to claim 1, wherein at least one of the sample inlet opening, the optical window, and the air outlet opening has a film which is configured to be removed before use of the sample collection unit.

10. The sample collection unit according to claim 1, wherein the optical window is surrounded by an opaque sealing lip.

11. The sample collection unit according to claim 1, wherein the sample collection unit is configured as a cartridge.

12. The sample collection unit according to claim 11, wherein the cartridge has catches configured to lock the cartridge onto at least one of a sampling unit and an analysis unit.

13. The sample collection unit according to claim 12, wherein the device configured to release the solvent has an actuation mechanism coupled to the catches.

14. A system for microbiological air analysis, comprising:
a sampling unit;
an analysis unit; and
a sample collection unit including:
    a housing having a sample inlet opening, an optical window, and an air outlet opening;
    a sample treatment path having a conjugation pad, and a test strip with a test area and an absorber section, the test area location between the conjugation pad and the absorber section along the sample treatment path;
    a device configured to receive a container for a solvent; and
    a device configured to release the solvent into the sample treatment path so as to move a sample from the conjugation pad to the test area,
wherein the sample collection unit is both part of the sampling unit and also part of the analysis unit.

15. A method for microbiological air analysis, comprising:
a) making available a sampling unit with a sample collection unit;
b) collecting particles in the sample collection unit;
c) building an analysis unit to the sample collection unit by aligning a sensor of the analysis unit with an optical window of a housing of the sample collection unit;
d) releasing a solvent in the sample collection unit;
e) transporting the collected particles into a test area within the housing with the solvent; and
f) analyzing the particles in the test area within the housing using the analysis unit.

* * * * *